United States Patent
Nakajima et al.

(10) Patent No.: US 11,653,876 B2
(45) Date of Patent: May 23, 2023

(54) CYCLIC ALTERNATIVE PATTERN (CAP) DETECTION DEVICE, CYCLIC ALTERNATIVE PATTERN (CAP) DETECTION METHOD, AND RECORDING MEDIUM

(71) Applicant: CASIO COMPUTER CO., LTD., Tokyo (JP)

(72) Inventors: Mitsuyasu Nakajima, Tokyo (JP); Kouichi Nakagome, Tokorozawa (JP); Takashi Yamaya, Fussa (JP); Yasushi Maeno, Ome (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 258 days.

(21) Appl. No.: 16/993,086

(22) Filed: Aug. 13, 2020

(65) Prior Publication Data
US 2021/0085241 A1    Mar. 25, 2021

(30) Foreign Application Priority Data
Sep. 19, 2019 (JP) .............................. JP2019-170827

(51) Int. Cl.
*A61B 5/00* (2006.01)
*A61B 5/16* (2006.01)
*A61B 5/0245* (2006.01)

(52) U.S. Cl.
CPC .......... *A61B 5/4812* (2013.01); *A61B 5/0245* (2013.01); *A61B 5/16* (2013.01); *A61B 5/4815* (2013.01); *A61B 5/7275* (2013.01)

(58) Field of Classification Search
None
See application file for complete search history.

(56) References Cited

U.S. PATENT DOCUMENTS

| | | | | |
|---|---|---|---|---|
| 5,430,029 A * | 7/1995 | Biella | ................ | A61K 31/5513 514/415 |
| 6,171,242 B1 * | 1/2001 | Amano | .................... | A61B 5/02 600/560 |

(Continued)

FOREIGN PATENT DOCUMENTS

| | | |
|---|---|---|
| JP | 2001061820 A | 3/2001 |
| JP | 2012065853 A | 4/2012 |

(Continued)

OTHER PUBLICATIONS

Terzano, et al., "CAP variables and arousals as sleep electroencephalogram markers for primary insomnia", Clinical Neurophysiology Sep. 2003; 114(9): 1715-23).

*Primary Examiner* — Carl H Layno
*Assistant Examiner* — Manolis Pahakis
(74) *Attorney, Agent, or Firm* — Holtz, Holtz & Volek PC (57) ABSTRACT

A CAP detection device configured to acquire pulse wave data of a subject, derive a baseline of the data and an envelope of the baseline, identify a local maximum point of the envelope and determine, as CAP candidate points, a first local maximum point of the baseline before the local maximum point of the envelope and a second local maximum point of the baseline after the local maximum point, and identify, for each CAP candidate point, a third local maximum point of the baseline before the CAP candidate point and a local minimum point of the baseline between the CAP candidate point and the third local maximum point and detect the CAP candidate point as a CAP based on an evaluation value obtained from a difference between the CAP candidate point and the third local maximum point and a difference between the CAP candidate point and the local minimum point.

5 Claims, 7 Drawing Sheets

(56) References Cited

U.S. PATENT DOCUMENTS

| | | | | |
|---|---|---|---|---|
| 6,599,242 B1* | 7/2003 | Splett | A61B 5/7232 | 345/440.1 |
| 7,324,845 B2* | 1/2008 | Mietus | A61B 5/0816 | 600/513 |
| 8,251,910 B2* | 8/2012 | Saito | A61B 5/7239 | 600/481 |
| 9,579,065 B2* | 2/2017 | Allavatam | A61B 5/341 | |
| 9,636,408 B2* | 5/2017 | Nebuloni | A61P 29/00 | |
| 10,835,132 B2* | 11/2020 | Qasem | A61B 5/02108 | |
| 11,006,842 B2* | 5/2021 | Qasem | A61B 5/02141 | |
| 11,478,184 B1* | 10/2022 | Dagum | A61B 5/7275 | |
| 2004/0220483 A1* | 11/2004 | Yeo | A61B 5/1455 | 128/920 |
| 2005/0245830 A1* | 11/2005 | Hutchinson | A61B 5/4818 | 600/483 |
| 2006/0178585 A1* | 8/2006 | Sharrock | A61B 5/412 | 600/490 |
| 2008/0302364 A1* | 12/2008 | Garde | A61M 16/026 | 128/204.23 |
| 2009/0306523 A1* | 12/2009 | Saito | A61B 5/7239 | 600/481 |
| 2010/0041966 A1* | 2/2010 | Kang | G16H 40/67 | 600/301 |
| 2011/0092831 A1* | 4/2011 | Herscovici-Cohen | A61B 5/4812 | 600/500 |
| 2011/0124656 A1* | 5/2011 | Seth | A61K 31/131 | 514/323 |
| 2011/0270097 A1* | 11/2011 | Aboy | A61B 5/4836 | 600/484 |
| 2011/0319389 A1* | 12/2011 | Lederman | G16C 99/00 | 514/561 |
| 2012/0179382 A1* | 7/2012 | Zhang | A61B 5/7264 | 702/19 |
| 2013/0079647 A1* | 3/2013 | McGonigle | A61B 5/7239 | 600/300 |
| 2013/0080119 A1* | 3/2013 | Khait | A61B 5/073 | 702/194 |
| 2013/0324859 A1* | 12/2013 | Park | A61B 5/02007 | 600/479 |
| 2014/0187941 A1* | 7/2014 | Shusterman | A61B 5/02116 | 600/480 |
| 2014/0228905 A1* | 8/2014 | Bolea | A61N 1/3611 | 607/42 |
| 2014/0323822 A1* | 10/2014 | Addison | A61B 5/0295 | 600/301 |
| 2015/0059755 A1* | 3/2015 | Bassin | A61B 5/4818 | 128/204.23 |
| 2015/0065894 A1* | 3/2015 | Airaksinen | A61B 5/7282 | 702/19 |
| 2015/0217082 A1* | 8/2015 | Kang | G16Z 99/00 | 600/27 |
| 2016/0213332 A1* | 7/2016 | Ukawa | A61B 5/7278 | |
| 2016/0338603 A1* | 11/2016 | Nakata | A61B 5/0022 | |
| 2017/0188993 A1* | 7/2017 | Hamilton | A61B 8/5223 | |
| 2017/0258436 A1* | 9/2017 | Kjær Thing Riknagel et al. | A61B 7/00 | |
| 2017/0281076 A1* | 10/2017 | Takahashi | A61B 5/02108 | |
| 2019/0200935 A1* | 7/2019 | Bandyopadhyay | G06K 9/00503 | |
| 2020/0008690 A1* | 1/2020 | Kokubo | A61B 5/4818 | |
| 2020/0037963 A1* | 2/2020 | Park | A61B 5/7282 | |
| 2020/0324114 A1* | 10/2020 | Chiapetta | A61N 1/37282 | |
| 2020/0375480 A1* | 12/2020 | Costa | A61B 5/024 | |
| 2021/0085256 A1* | 3/2021 | Nakajima | A61B 5/4812 | |
| 2021/0330203 A1* | 10/2021 | Xu | A61B 5/14542 | |
| 2021/0338973 A1* | 11/2021 | Poltorak | A61B 5/165 | |
| 2021/0369192 A1* | 12/2021 | Goldstein | A61B 5/741 | |
| 2022/0039742 A1* | 2/2022 | Hilmisson | A61B 5/14551 | |
| 2022/0241264 A1* | 8/2022 | Weinberg | A61K 31/404 | |
| 2022/0265170 A1* | 8/2022 | Yabusaki | A61B 5/14546 | |
| 2022/0323000 A1* | 10/2022 | Huang | A61B 5/4809 | |
| 2022/0386946 A1* | 12/2022 | Hilmisson | A61B 5/4812 | |
| 2022/0387749 A1* | 12/2022 | Poltorak | A61M 21/02 | |

FOREIGN PATENT DOCUMENTS

| | | |
|---|---|---|
| JP | 2012090913 A | 5/2012 |
| WO | 2016035460 A1 | 3/2016 |

\* cited by examiner

CYCLIC ALTERNATIVE PATTERN (CAP) DETECTION DEVICE, CYCLIC ALTERNATIVE PATTERN (CAP) DETECTION METHOD, AND RECORDING MEDIUM

PRIORITY CLAIM BASED ON EARLIER APPLICATION

[Application Number] Japanese Patent Application No. 2019-170827
[Application Date] Sep. 19, 2019

BACKGROUND

1. Technical Field

The present disclosure relates to a technique for detecting a cyclic alternative pattern (CAP).

2. Related Art

As a sleep state monitoring system for determining a sleep state, determination of sleep stages (light sleep, deep sleep, REM sleep, non-REM sleep, and the like) based on an electroencephalogram has been widely used (for example, JP 2011-83393 A). In addition, a sleep monitoring system using body movements and pulse waves that are easier to acquire than brain waves has also been proposed (for example, JP 2018-161432 A).

Meanwhile, the sleep stages are used as one sleep index, but it cannot be said that its correlation with the sleep subjectivity indicating the sleep satisfaction of a subject is high. For this reason, as a sleep index having a high correlation with the sleep subjectivity, a cyclic alternative pattern (CAP) defined based on an electroencephalogram is known (for example, Terzano M G, Parrino L, Spaggiari M C, Palomba V, Rossi M, Smerieri A, et al. CAP variables and arousals as sleep electroencephalogram markers for primary insomnia. Clin Neurophysiol 2003 September; 114(9): 1715-23). In general, sleep quality is poor in a period of high CAP frequency.

SUMMARY

In order to solve the above problem, an aspect of the present disclosure relates to a cyclic alternative pattern (CAP) detection device including a memory storing a program, and at least one processor configured to execute the program stored in the memory, in which the processor is configured to: acquire pulse wave data of a subject; derive a baseline of the pulse wave data and an envelope of the baseline; identify a local maximum point of the envelope and determine, as CAP candidate points each indicating a cyclic alternative pattern, a first local maximum point of the baseline before the local maximum point of the envelope and a second local maximum point of the baseline after the local maximum point of the envelope on a time axis; and identify, for each of the identified CAP candidate points, a third local maximum point of the baseline before the CAP candidate point and a local minimum point of the baseline between the CAP candidate point and the third local maximum point and detect the CAP candidate point as a CAP based on an evaluation value obtained from a difference between the CAP candidate point and the third local maximum point and a difference between the CAP candidate point and the local minimum point.

In order to solve the above problem, another aspect of the present disclosure relates to a CAP detection device including a memory storing a program, and at least one processor configured to execute the program stored in the memory, in which the processor is configured to: acquire pulse wave data of a subject; derive a baseline of the pulse wave data and an envelope of the baseline; identify a local maximum point of the envelope and determine, as CAP candidate points each indicating a cyclic alternative pattern, a first local minimum point of the baseline before the local maximum point of the envelope and a second local minimum point of the baseline after the local maximum point of the envelope on a time axis; and identify, for each of the identified CAP candidate points, a third local minimum point of the baseline before the CAP candidate point and a local maximum point of the baseline between the CAP candidate point and the third local minimum point and detect the CAP candidate point as a CAP based on an evaluation value obtained from a difference between the CAP candidate point and the third local minimum point and a difference between the CAP candidate point and the local maximum point.

DETAILED DESCRIPTION

The following embodiment discloses a cyclic alternative pattern (CAP) detection device that detects a CAP from pulse wave data during sleep of a subject.

SUMMARY OF THE PRESENT DISCLOSURE

Figure 1:
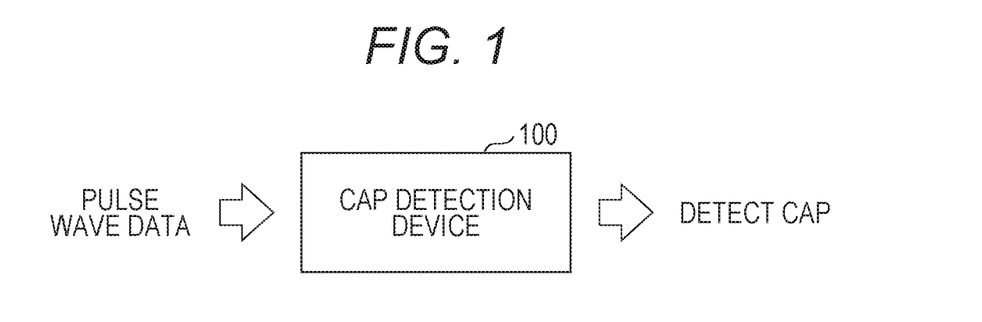
FIG. 1 is a schematic diagram showing a CAP detection device according to an embodiment of the present disclosure.

In summarizing the embodiment to be described below, as shown in FIG. 1, a CAP detection device 100 derives, when acquiring pulse wave data during sleep of a subject, the baseline of the acquired pulse wave data and the envelope of the baseline and detects a CAP, which is a sleep index adequately expressing sleep subjectivity, using inflection points of the derived baseline and envelope.

In this manner, the CAP detection device 100 is capable of detecting a CAP in consideration of the sleep subjectivity of a subject based on pulse wave data collected in time series from the sleeping subject using a pulse wave sensor that is easy to wear, instead of electroencephalogram data that is relatively difficult to acquire.

[Hardware Configuration]

Figure 2:
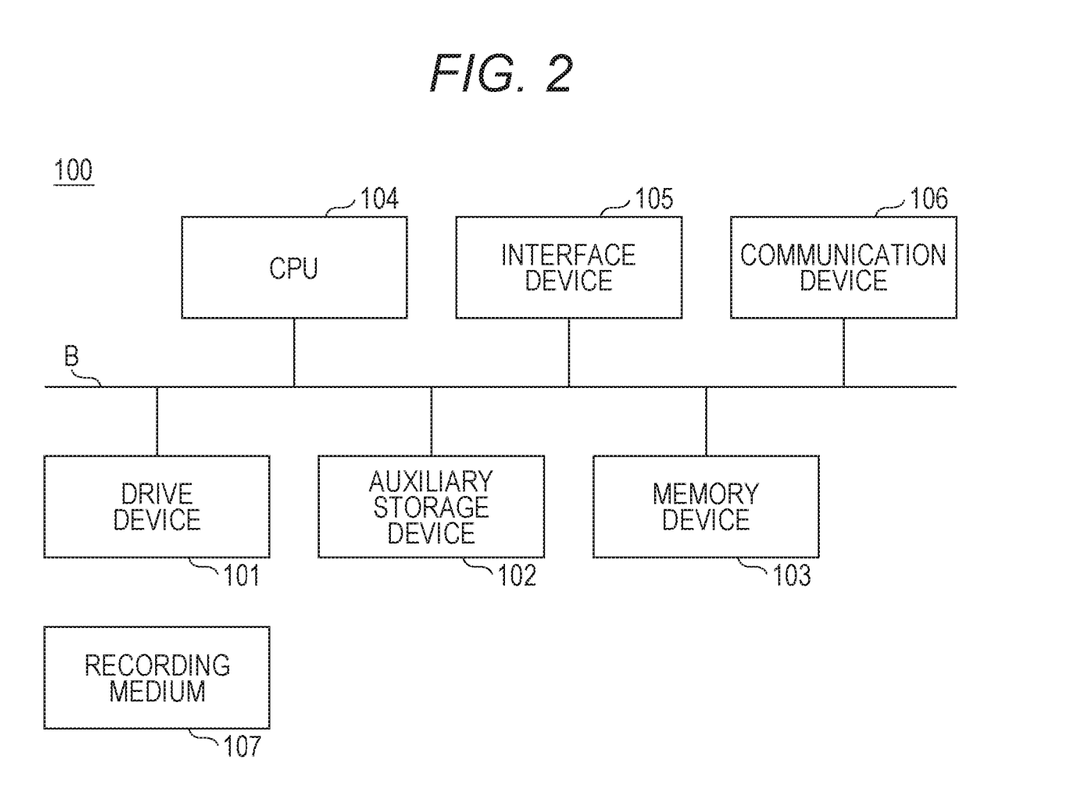
FIG. 2 is a block diagram showing a hardware configuration of a CAP detection device according to an embodiment of the present disclosure.

Here, the CAP detection device 100 may be a computing device, such as a server, be mounted on a pulse wave measurement device, such as a wrist device that performs measuring on a wrist, an ear device that performs measuring on an ear, or the like, or be a smartphone, a tablet, or the like that is communicatively connected to the pulse wave measuring device, and may have a hardware configuration as shown in FIG. 2. That is, the CAP detection device 100 includes a drive device 101, an auxiliary storage device 102, a memory device 103, a central processing unit (CPU) 104, an interface device 105, and a communication device 106 that are interconnected via a bus B.

Various computer programs including programs or instructions that perform various functions and processes to be described below of the CAP detection device 100 may be provided by a recording medium 107, such as a compact disk-read only memory (CD-ROM). When the recording medium 107 storing the programs is set in the drive device 101, the programs are installed in the auxiliary storage device 102 from the recording medium 107 via the drive device 101. However, the programs may not be necessarily installed by the recording medium 107, and may be downloaded from any external device via a network or the like. The auxiliary storage device 102 stores the installed programs and necessary files and data. The memory device 103 reads and stores the programs and data from the auxiliary storage device 102 when a program activation instruction is given. The auxiliary storage device 102 and the memory device 103 are implemented as non-transitory computer-readable storage media that stores programs or instructions. The CPU 104 that functions as at least one processor performs various functions and processes of the CAP detection device 100 according to various data, such as programs stored in the memory device 103 and parameters necessary for executing the programs. The interface device 105 is used as a communication interface for connecting to a network or an external device. The communication device 106 performs various communication processes for communicating with an external device. At least one of the interface device 105 and the communication device 106 functions as a pulse-wave-data acquisition unit that acquires pulse wave data of a subject from a pulse wave sensor to be described later or a wearable device equipped with the pulse wave sensor.

However, the CAP detection device 100 is not limited to the hardware configuration described above, may be implemented by, for example, any other appropriate hardware configuration, such as one or more circuits that perform one or more of the functions and processes of the CAP detection device 100, and may be implemented as, for example, a wristwatch-type wearable device to be worn on the subject's arm, an earphone-type hearable device to be inserted into the subject's ear, or a smartphone.

[CAP Detection Device]

Figure 3:
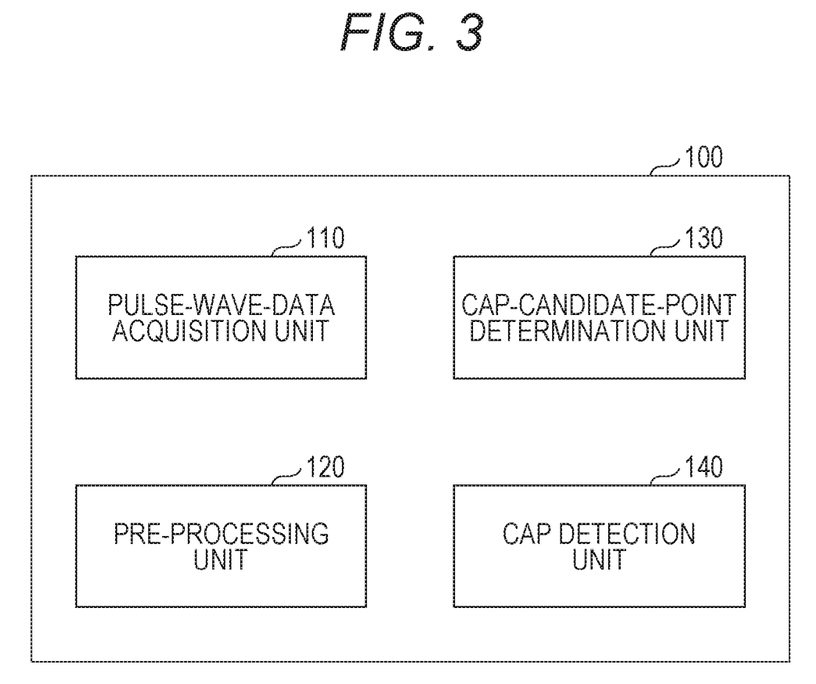
FIG. 3 is a block diagram showing a functional configuration of a CAP detection device according to an embodiment of the present disclosure.

Next, the CAP detection device 100 according to an embodiment of the present disclosure is described with reference to FIG. 3. FIG. 3 is a block diagram showing a functional configuration of the CAP detection device 100 according to an embodiment of the present disclosure.

As shown in FIG. 3, the CAP detection device 100 includes a pulse-wave-data acquisition unit 110, a pre-processing unit 120, a CAP-candidate-point determination unit 130, and a CAP detection unit 140.

Figure 4A:
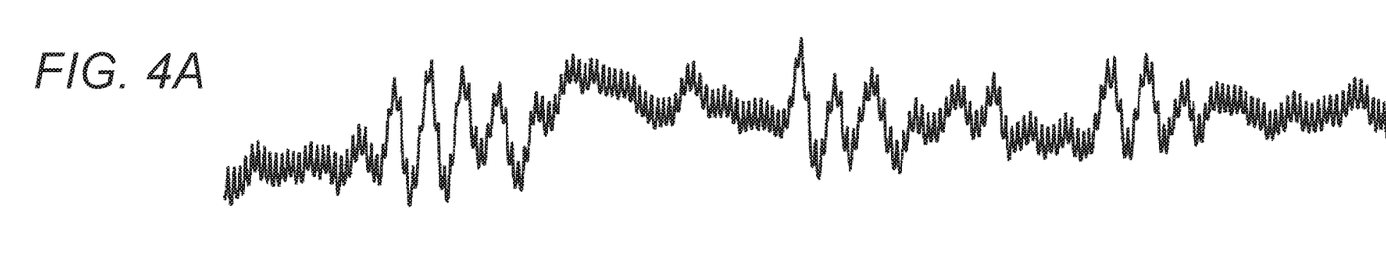
FIGS. 4A to 4C are schematic diagrams showing a pre-process for pulse wave data according to an embodiment of the present disclosure.

The pulse-wave-data acquisition unit 110 acquires pulse wave data of a subject. Specifically, the pulse wave data is collected from the sleeping subject by a wearable device equipped with a pulse wave sensor and provided to the CAP detection device 100. For example, the pulse wave data may be the data as shown in FIG. 4A. Here, the vertical axis represents the output of the pulse wave sensor, and the horizontal axis represents time. The output of the pulse wave sensor repeatedly increases and decreases in a cycle of about one second and represents pulses.

For example, the pulse wave sensor may be implemented by various sensor, such as a sensor that detects a volume pulse wave by photoplethysmography (PPG), a Doppler blood flow meter that detects a blood flow pulse wave, and a piezoelectric sensor that detects a pressure pulse wave.

The pulse-wave-data acquisition unit 110 provides the pulse wave data acquired from the pulse wave sensor to the pre-processing unit 120.

Figure 4B:
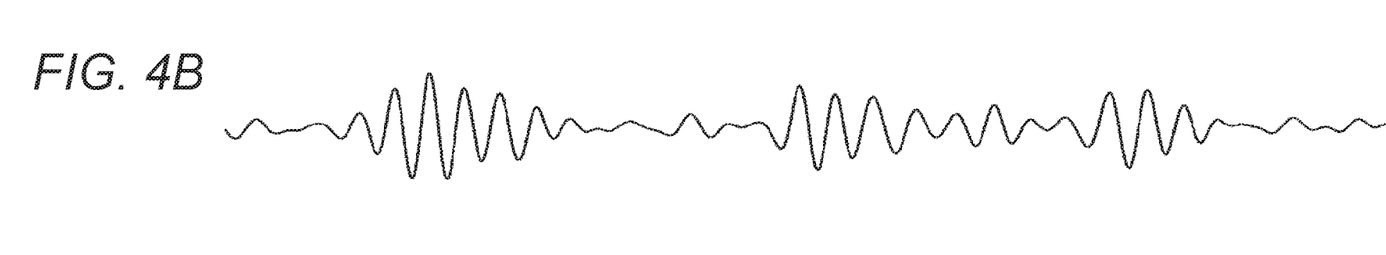

The pre-processing unit 120 derives the baseline of the pulse wave data and the envelope of the baseline. Specifically, when acquiring the pulse wave data as shown in FIG. 4A from the pulse-wave-data acquisition unit 110, the pre-processing unit 120 performs a bandpass filter process on the acquired pulse wave data and derives the baseline of the pulse wave data as shown in FIG. 4B. For example, the band pass filter process may be for extracting a range of, for example, 0.08 Hz to 0.2 Hz from the pulse wave data acquired from the pulse-wave-data acquisition unit 110.

Figure 4C:
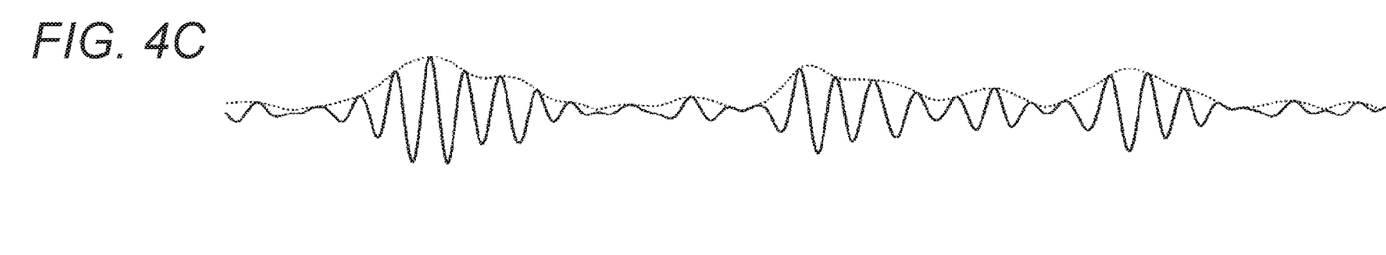

After deriving the baseline in this manner, the pre-processing unit 120 further derives the envelope of the derived baseline. For example, the pre-processing unit 120 may acquire the envelope by performing the Hilbert transform on the derived baseline, and the envelope indicated by the dashed line in FIG. 4C can be acquired for the baseline in FIG. 4B.

After deriving the baseline and the envelope in this manner, the pre-processing unit 120 provides the derived baseline and envelope to the CAP-candidate-point determination unit 130.

The CAP-candidate-point determination unit 130 identifies the local maximum point of the envelope and determines, as CAP candidate points, a first local maximum point of the baseline before the local maximum point of the envelope and a second local maximum point of the baseline after the local maximum point of the envelope on the time axis. When a CAP occurs, a large pulse wave change occurs a few seconds after the CAP, regardless of the length of the CAP. A CAP point is the position where the large pulse wave change occurs, and a CAP candidate point is a candidate thereof. Specifically, the CAP-candidate-point determination unit 130 first identifies one or more local maximum points of the envelope acquired from the pre-processing unit 120. For example, the CAP-candidate-point determination unit 130 identifies a plurality of local maximum points indicated by dots on the envelope in FIG. 5 for the envelope indicated by the broken line in FIG. 4C. The use of the envelope makes it possible to effectively extract the number of CAP candidate points suitable for the CAP interval, which is considered to be within the range of 20 to 40 seconds, and to detect a robust and highly-accurate CAP.

When identifying the local maximum points of the envelope, the CAP-candidate-point determination unit 130 identifies the CAP candidate points for each of the determined local maximum points. Specifically, the CAP-candidate-point determination unit 130 identifies, for the local maximum point A1 of the envelope shown in FIG. 5, the local maximum points K1 and K2 of the baseline before and after the local maximum point A1 on the time axis and determines the identified local maximum points K1 and K2 as the CAP candidate points for the local maximum point A1. In other words, the CAP candidate points K1 and K2 for the local maximum point A1 are the local maximum points of the baseline that sandwiches the local maximum point A1 on the time axis. The CAP-candidate-point determination unit 130 performs the above CAP-candidate-point determination process on all the identified local maximum points and holds the identified local maximum points of the baseline as the CAP candidate points.

The CAP detection unit 140 identifies, for each of the determined CAP candidate points, the local maximum point of the baseline before the CAP candidate point and the local minimum point of the baseline between the CAP candidate point and the preceding local maximum point on the time axis and detects the CAP candidate point as a CAP based on an evaluation value calculated from the difference between the CAP candidate point and the preceding local maximum point and the difference between the CAP candidate point and the local minimum point. Here, the CAP is defined by a sudden change in frequency and amplitude of an electroencephalogram. The CAP is caused by cortical arousal (arousal by the cortex on the surface of the cerebrum). The cortical arousal is an autonomic nervous activity and affects the contraction of peripheral blood vessels. That is, when a CAP occurs, it is said that an autonomic nerve activity causes an increase in heartbeat, an increase in blood pressure, a disturbance in the pulse baseline, respiratory variation, a decrease in pulse wave amplitude, the occurrence of body movement, and the like. The disturbance in the pulse baseline, the increase in heartbeat, and the decrease in pulse wave amplitude (pulse wave height) were examined from the pulse wave by experiments, and it was found that the correlations with the CAP were high in this order. FIG. 4A is an example in which three CAPs occur.

Figure 5:
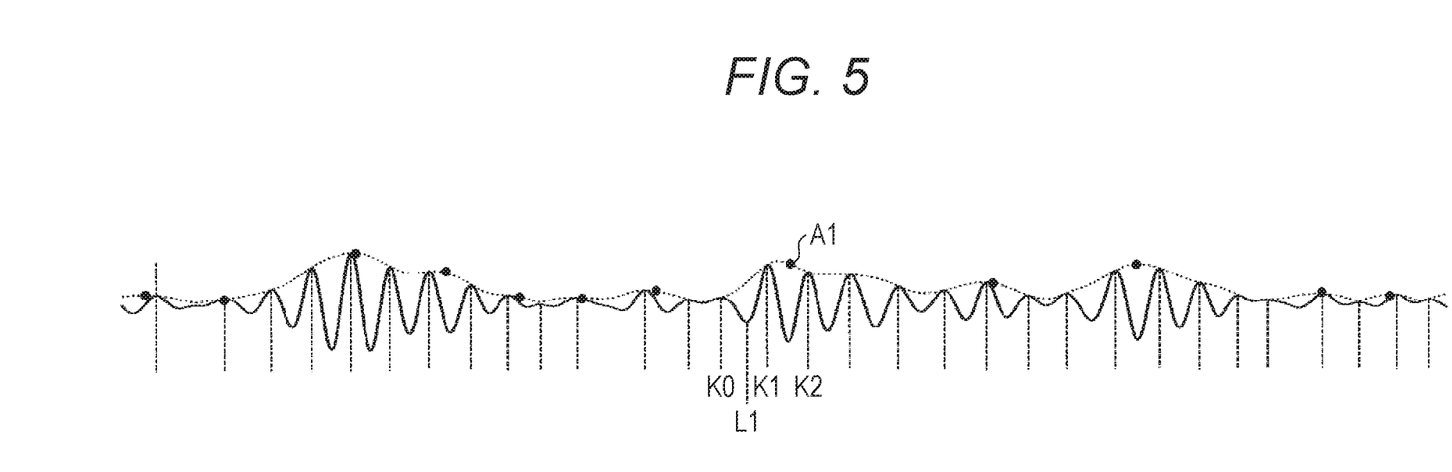
FIG. 5 is a schematic diagram showing a CAP detection process according to an embodiment of the present disclosure.

Specifically, the CAP detection unit 140 identifies, for the CAP candidate point K1 shown in FIG. 5, the preceding local maximum point K0 of the baseline on the time axis and the local minimum point L1 of the baseline between K1 and K0. When identifying the local maximum point K0 and the local minimum point L1 of the baseline, the CAP detection unit 140 subtracts the baseline value at K0 from the baseline value at K1 to calculate the difference B0. However, if the difference is negative, the difference B0 is set to zero. The CAP detection unit 140 further subtracts the baseline value at L1 from the baseline value at K1 to calculate the difference B1. However, if the difference is negative, the difference B1 is set to zero. After calculating these differences B0 and B1, the CAP detection unit 140 calculates B0*th0+B1*th1 and sets the calculated value as an evaluation value C. Here, th0 and th1 represent predetermined positive thresholds. In addition, th0>th1 may be set.

Similarly, the CAP detection unit 140 calculates the evaluation value C for the CAP candidate point K2, compares the evaluation values C for K1 and K2, and identifies the CAP candidate point K1 or K2 having a larger evaluation value C. Then, the CAP detection unit 140 determines whether the evaluation value C for the identified CAP candidate point is equal to or higher than a threshold Th and determines, when the evaluation value C is equal to or higher than the threshold Th, the CAP candidate point as the CAP for the local maximum point A1 of the envelope. On the other hand, when the evaluation value C is less than the threshold Th, the CAP detection unit 140 determines that the CAP corresponding to the local maximum point A1 of the envelope has not been detected, that is, determines that the CAP candidate point is a non-CAP.

In an embodiment, the CAP detection unit may calculate the difference between the maximum pulse rate and the minimum pulse rate in the period between the local maximum point K0 of the baseline before the CAP candidate point K1 and the CAP candidate point K1 and determine, when the difference is equal to or less than a predetermined threshold th2, the CAP candidate point K1 as a non-CAP. Since the pulse wave sensor observes different waveforms depending on the measurement positions, the baseline change is assumed to be clear when the pulse wave is measured on, for example, a fingertip, and the threshold th2 may be set to zero. Meanwhile, a baseline change tends to be buried in noise when the pulse wave is measured on the earlobe, and the threshold th2 may be set to any appropriate positive number (for example, th2=3). When the difference between the maximum pulse rate and the minimum pulse rate is equal to or less than the threshold th2, it is considered that the variation of the pulse rate in the period can be noise, and the CAP candidate point may be determined as a non-CAP.

Although the pulse rate has been used as the pulse wave data in the above embodiment, the pulse wave data according to the present disclosure is not limited thereto and may be the pulse wave height indicating the height of one beat. Alternatively, both the pulse rate and the pulse wave height may be used.

[CAP Detection Process]

Figure 6:
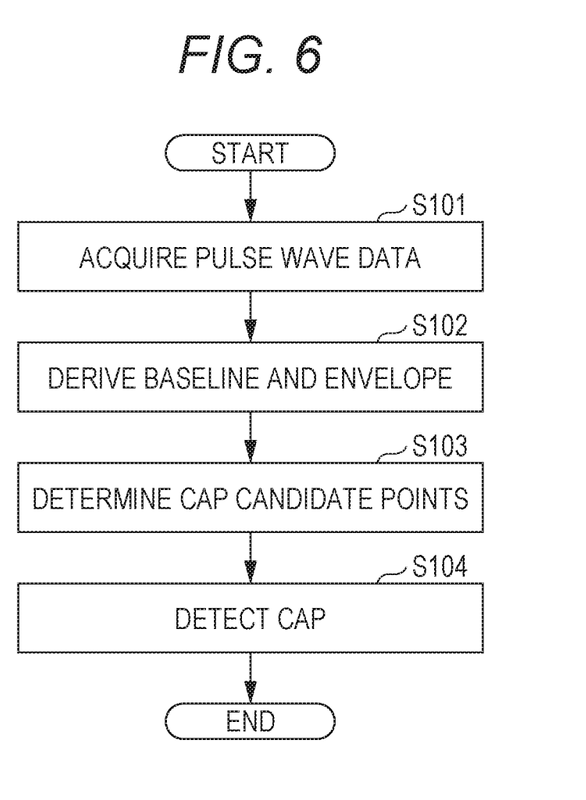
FIG. 6 is a flowchart showing an entire process of a CAP detection device according to an embodiment of the present disclosure.
Figure 7:
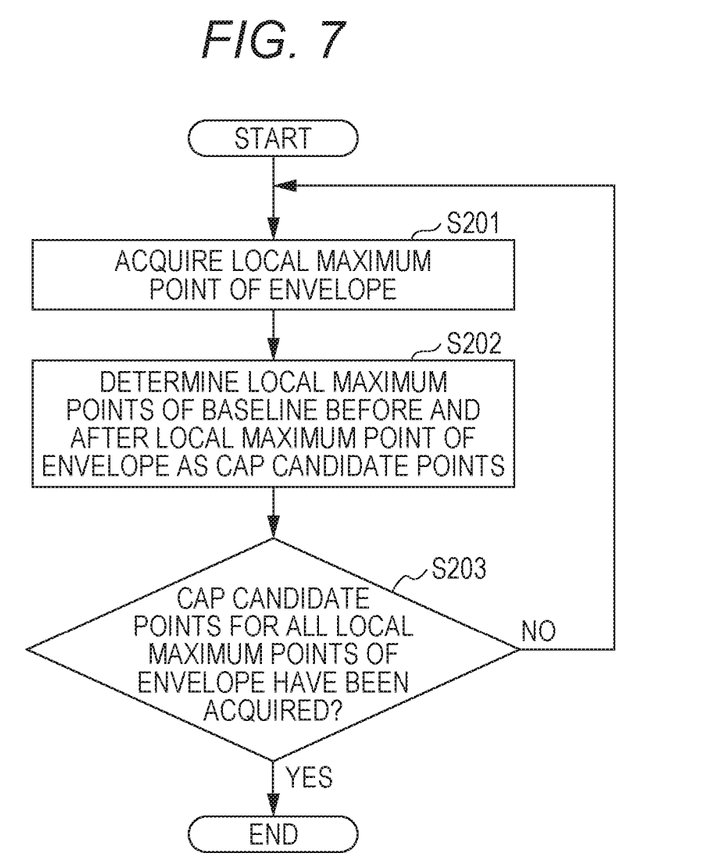
FIG. 7 is a flowchart showing details of a CAP-candidate-point determination process according to an embodiment of the present disclosure.
Figure 8:
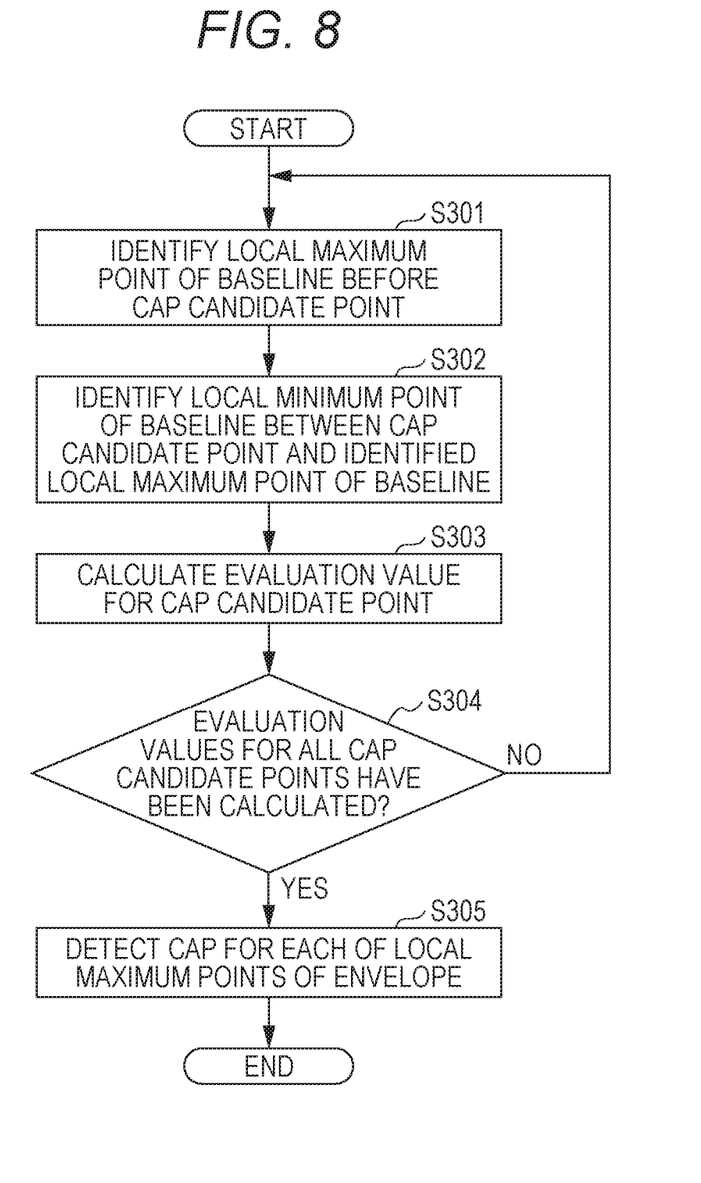
FIG. 8 is a flowchart showing details of a CAP detection process according to an embodiment of the present disclosure.

Next, a CAP detection process according to an embodiment of the present disclosure is described with reference to FIGS. 6 to 8. The CAP detection process is performed by the CAP detection device 100 described above and may be performed by, for example, the processor of the CAP detection device 100 executing a program or an instruction. FIG. 6 is a flowchart showing an entire CAP detection process according to an embodiment of the present disclosure. FIG. 7 is a flowchart showing details of a CAP-candidate-point determination process according to an embodiment of the present disclosure, and FIG. 8 is a flowchart showing details of a CAP detection process according to an embodiment of the present disclosure.

As shown in FIG. 6, in step S101, the CAP detection device 100 acquires pulse wave data. Specifically, the CAP detection device 100 acquires pulse wave data, such as the pulse rate or the pulse wave height during sleep of a subject collected by the pulse wave sensor.

In step S102, the CAP detection device 100 derives the baseline and envelope of the pulse wave data. Specifically, the CAP detection device 100 performs a pre-process, such as a bandpass filter process, on the pulse wave data acquired in step S101 to derive the baseline of the pulse wave data. Note that, the CAP detection device 100 may acquire, instead of the pulse wave data, the baseline derived from the pulse wave data. In addition, the CAP detection device 100 performs the Hilbert transform on the derived baseline to derive the envelope of the baseline. Note that, the CAP detection device 100 may acquire, instead of the pulse wave data, the baseline and envelope derived from the pulse wave data.

In step S103, the CAP detection device 100 determines CAP candidate points. The details of the CAP-candidate-point determination process in step S103 according to an embodiment of the present disclosure are described with reference to FIG. 7.

As shown in FIG. 7, in step S201, the CAP detection device 100 acquires the local maximum point of the envelope derived in step S102. For example, the CAP detection device 100 identifies A1 shown in FIG. 5 as the local maximum point of the envelope.

In step S202, the CAP detection device 100 identifies the local maximum points of the baseline before and after the identified local maximum point of the envelope on the time axis, that is, the two local maximum points of the baseline sandwiching the local maximum point of the envelope on the time axis and determines the identified local maximum points of the baseline as CAP candidate points. For example, the CAP detection device 100 identifies K1 and K2 shown in FIG. 5 as the local maximum points of the baseline before and after A1 on the time axis and determines K1 and K2 as the CAP candidate points.

In step S203, the CAP detection device 100 determines whether the CAP candidate points for all the local maximum points of the envelope have been acquired. When the CAP candidate points for all the local maximum points of the envelope have been acquired (S203: YES), the CAP detection device 100 proceeds to step S104. On the other hand, when the CAP candidate points for all the local maximum points of the envelope have not been acquired (S203: NO), the CAP detection device 100 returns to step S201 and acquires other local maximum points of the envelope to repeat the CAP-candidate-point determination process.

In step S104, the CAP detection device 100 detects a CAP from the CAP candidate points. The details of the CAP detection process in step S104 according to an embodiment of the present disclosure are described with reference to FIG. 8.

As shown in FIG. 8, in step S301, the CAP detection device 100 identifies the local maximum point of the baseline before the CAP candidate point on the time axis. For example, the CAP detection device 100 extracts, for the CAP candidate point K1, K0 shown in FIG. 5 as the local maximum point of the baseline before K1.

In step S302, the CAP detection device 100 identifies the local minimum point of the baseline between the local maximum point of the baseline before the CAP candidate point extracted in step S301 and the CAP candidate point. For example, the CAP detection device 100 extracts L1 shown in FIG. 5 as the local minimum point of the baseline.

In step S303, the CAP detection device 100 calculates the evaluation value for the CAP candidate point. For example, for the CAP candidate point K1, the CAP detection device 100 subtracts the baseline value at the local maximum point K0 of the baseline from the baseline value at the CAP candidate point K1 to calculate the difference B0. However, when the difference is negative, the difference B0 is set to zero. In addition, the CAP detection device 100 subtracts the baseline value at the local minimum point L1 of the baseline from the baseline value at the CAP candidate point K1 to calculate the difference B1. However, when the difference is negative, the difference B1 is set to zero. Then, the CAP detection device 100 calculates B0*th0+B1*th1 and sets the calculated value as the evaluation value C for the CAP candidate point K1. Here, th0 and th1 represent predetermined positive thresholds. In addition, th0>th1 may be set.

In step S304, the CAP detection device 100 determines whether the evaluation values for all the CAP candidate points determined in step S103 have been calculated. When the evaluation values for all the CAP candidate points have been calculated (S304: YES), the CAP detection device 100 detects a CAP for each of the local maximum points of the envelope in step S305. For example, the CAP detection device 100 compares the evaluation values C for the CAP candidate points K1 and K2 for the local maximum point A1 of the envelope and determines whether the evaluation value C for the CAP candidate point having a higher evaluation value is equal to or higher than the predetermined threshold Th. When the evaluation value C is equal to or higher than the predetermined threshold Th, the CAP detection device 100 determines that a CAP has occurred at the CAP candidate point. On the other hand, when the evaluation value C is less than the predetermined threshold Th, the CAP detection device 100 determines that no CAP has occurred at the CAP candidate point. The CAP detection device 100 performs the process on all the local maximum points of the envelope and determines whether a CAP has occurred at each of the local maximum points of the envelope.

On the other hand, when the evaluation values for all the CAP candidate points have not been calculated (S304: NO), the CAP detection device 100 returns to step S301 and repeats steps S301 to S304 described above.

The thresholds th0, th1, th2, and Th may be set to appropriate values according to the type of the pulse wave sensor and/or the measurement position. In this embodiment, K0, K1, and K2 are local maximum values, and L1 is a local minimum value. This assumes that the pulse wave acquisition system has a larger value when the blood vessel contracts. This is when a signal is on the plus side when the blood vessel contracts in the case of a PPG method using as the pulse wave acquisition system, and is when a signal is in the plus direction when the blood flow becomes slow in the case of a blood flow sensor. When the configuration of the pulse wave acquisition system is different, the CAP detection device 100 needs to determine whether to take a local maximum value or a local minimum value depending on the signal change direction when the blood vessel contracts. Note that, A1 takes a local maximum value of the envelope, regardless of the pulse wave acquisition system.

The invention of the present application is not limited to the above embodiments and can be variously modified in a practical phase without departing from the spirit of the invention. In addition, the respective embodiments may be appropriately combined as much as possible, and the combined effects can be obtained in that case. Furthermore, the above embodiments include inventions at various phases, and various inventions can be extracted by appropriately combining a plurality of disclosed constituent elements. For example, as long as the problem described above can be solved and the effects described above can be obtained although some constituent elements are deleted from all the constituent elements described in the embodiments, the configuration in which these constituent elements are deleted can be extracted as the invention.

What is claimed is:

1. A cyclic alternative pattern (CAP) estimation device comprising:
   a pulse wave sensor;
   a memory storing a program; and
   at least one processor configured to execute the program stored in the memory,
   wherein the processor is configured to:
      acquire, from the pulse wave sensor, pulse wave data of a subject;
      derive a baseline of the pulse wave data and an envelope of the baseline;
      identify a local maximum point of the envelope and determine, as CAP candidate points each indicating a cyclic alternative pattern, (i) a first local maximum point of the baseline before the local maximum point of the envelope on a time axis and (ii) a second local maximum point of the baseline after the local maximum point of the envelope on the time axis;

for each of the identified CAP candidate points, identify a third local maximum point of the baseline before the CAP candidate point and a local minimum point of the baseline between the CAP candidate point and the third local maximum point, and obtain an evaluation value from (i) a difference between the CAP candidate point and the third local maximum point and (ii) a difference between the CAP candidate point and the local minimum point, and estimate one of the identified CAP candidate points as a CAP by comparing the obtained evaluation values for each of the identified CAP candidate points and a threshold.

2. The CAP estimation device according to claim 1, wherein the processor is configured to determine a CAP candidate point having a larger evaluation value, from among the evaluation value of the first local maximum point and the evaluation value of the second local maximum point, as a CAP for the local maximum point of the envelope.

3. The CAP estimation device according to claim 1, wherein the processor is configured to, for each of the identified CAP candidate points, acquire a difference between a maximum pulse rate and a minimum pulse rate in a period between the third local maximum point and the CAP candidate point and determine, if the difference is equal to or less than a predetermined threshold, the CAP candidate point as a non-CAP.

4. A cyclic alternative pattern (CAP) estimation method of a CAP estimation device comprising a pulse wave sensor and at least one processor, the method being performed by the at least one processor, and the method comprising:

acquiring, from the pulse wave sensor, pulse wave data of a subject;

deriving a baseline of the pulse wave data and an envelope of the baseline;

identifying a local maximum point of the envelope and determining, as CAP candidate points each indicating a cyclic alternative pattern, (i) a first local maximum point of the baseline before the local maximum point of the envelope on a time axis and (ii) a second local maximum point of the baseline after the local maximum point of the envelope on the time axis;

for each of the identified CAP candidate points, identifying a third local maximum point of the baseline before the CAP candidate point and a local minimum point of the baseline between the CAP candidate point and the third local maximum point, and obtaining an evaluation value from (i) a difference between the CAP candidate point and the third local maximum point and (ii) a difference between the CAP candidate point and the local minimum point; and estimating one of the identified CAP candidate points as a CAP by comparing the obtained evaluation values for each of the identified CAP candidate points and a threshold.

5. A non-transitory computer-readable recording medium comprising a program stored thereon which, when executed by at least one processor of a cyclic alternative pattern (CAP) estimation device comprising a pulse wave sensor and the at least one processor, causes the at least one processor to:

acquire, from the pulse wave sensor, pulse wave data of a subject;

derive a baseline of the pulse wave data and an envelope of the baseline;

identify a local maximum point of the envelope and determine, as CAP candidate points each indicating a cyclic alternative pattern, (i) a first local maximum point of the baseline before the local maximum point of the envelope on a time axis and (ii) a second local maximum point of the baseline after the local maximum point of the envelope on the time axis;

for each of the identified CAP candidate points, identify a third local maximum point of the baseline before the CAP candidate point and a local minimum point of the baseline between the CAP candidate point and the third local maximum point, and obtain an evaluation value from (i) a difference between the CAP candidate point and the third local maximum point and (ii) a difference between the CAP candidate point and the local minimum point; and estimate one of the identified CAP candidate points as a CAP by comparing the obtained evaluation values for each of the identified CAP candidate points and a threshold.

* * * * *